United States Patent [19]
Fogel

[11] Patent Number: 6,159,944
[45] Date of Patent: *Dec. 12, 2000

[54] METHOD FOR TREATING PAINFUL CONDITIONS OF THE ANAL REGION AND COMPOSITIONS THEREFOR

[75] Inventor: Barry S. Fogel, Providence, R.I.

[73] Assignee: Synchroneuron, LLC, Waban, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 09/031,858

[22] Filed: Feb. 27, 1998

[51] Int. Cl.⁷ .................................................. A61K 31/70
[52] U.S. Cl. .............................. 514/27; 514/716; 514/626
[58] Field of Search ................................ 514/27, 716, 626

[56] References Cited

U.S. PATENT DOCUMENTS

| | | |
|---|---|---|
| 4,945,084 | 7/1990 | Packman . |
| 5,504,117 | 4/1996 | Gorfine . |
| 5,595,753 | 1/1997 | Hechtman . |
| 5,693,676 | 12/1997 | Gorfine . |

*Primary Examiner*—Rebecca Cook
*Attorney, Agent, or Firm*—Choate, Hall & Stewart

[57] ABSTRACT

Method and composition for treating painful conditions of the body, particularly the anal region. The compositions include a combination of nitroglycerin and sucralfate or a combination of nitroglycerin, lidocaine and sucralfate. The compositions may be included in a petrolatum base along with a water soluble lubricant. These compositions have been found effective in treating painful conditions in the anal region, such as anal fissures, inflamed or recently thrombosed hemorrhoids, and other chronic anal pain.

16 Claims, No Drawings

METHOD FOR TREATING PAINFUL CONDITIONS OF THE ANAL REGION AND COMPOSITIONS THEREFOR

BACKGROUND OF THE INVENTION

This invention relates to methods and compositions for treating painful conditions of the anal region and more particularly for treating anal fissures, thrombosed or inflamed hemorrhoids, for pain associated with ligation of internal hemorrhoids and for chronic anal pain.

Anal fissures can be an extremely painful condition. The primary reason for severe pain is spasm of the anal sphincter. This spasm causes ischemia, which both produces pain and interferes with healing (Sharp, American Journal of Surgery, 1996; Volume 171, pages 512–515; Schouten et al., 1993, Scandinavian Journal of Gastroenterology, Volume 31, Supplement 218, pp. 78–81). Spasm of the anal sphincter also plays a role in the pain of inflammatory conditions of the anal region, such as inflamed or recently thrombosed hemorrhoids (Janicke & Pundt, 1996, Emergency Medicine Clinics of North America, Volume 14, pp. 757–788). See also, Madoff, R D., "Pharmacologic Therapy for Anal Fissure," New England Journal of Medicine January 1998 22:338(4) 217–20.

Effective treatments for anal fissures, whether medical or surgical, involve relaxation of the spastic muscle. These treatments include lateral sphincterotomy, injection of the sphincter with botulinum toxin, and application of nitroglycerin ointment. A recent review by Sharp of treatment for chronic anal fissures recommends beginning with nitroglycerin ointment. If the fissure has not healed in six weeks, botulinum toxin injections are given. That review notes that "considerable educational effort is required to successfully adjust the dose" of nitroglycerin (Sharp, 1996, ibid.). It states that nitroglycerin "will often eliminate the severe pain of fissure-in-ano in 1 day". Schouten et al. (1993, ibid.) used topical isosorbide dinitrate to treat chronic anal fissures, attaining pain relief" within 10 days". Lund & Scholefield (1997, Lancet, Volume 349, pp. 11–14) reported a randomized controlled trial of 0.2% nitroglycerin ointment for anal fissure. At 2 weeks, pain on defecation, as measured by a visual analogue scale (0=no pain, 100=worst pain ever), averaged 33.5 in the treated group, compared with 48.0 in a group treated with placebo, and 73.0 in the same patients at baseline.

Nitroglycerin also has been reported to diminish the pain of thrombosed external hemorrhoids (Gorfine S R 1995, Diseases of the Colon and Rectum, Volume 38, p. 453).

Despite positive clinical trials, nitroglycerin has not been universally accepted as a treatment for anal fissure. According to an experienced rectal surgeon and a gastroenterologist with a special interest in the colon and rectum in a personal communication, many patients simply do not get adequate pain relief from nitroglycerin, even in concentrations as high as 0.5%. My experience with one patient was that nitroglycerin relieved the pain, but only in a concentration that caused a significant headache. Moreover, the patient's anal pain recurred within two hours. The review cited above points out additional problems, including the full day sometimes needed before pain is relieved, and compliance problems because of headaches and the need for frequent dosage adjustments (Sharp, 1996, ibid.). The problems of inadequate relief, short duration of relief, and intolerance of the drug were also described in a recent prospective study of 19 outpatients with chronic anal fissure (Watson et al., 1996, British Journal of Surgery, Volume 83, pp. 771–775). In this study, of the 15 patients who used nitroglycerin for 6 weeks and returned for a second visit, only 6 were symptom-free.

Lidocaine, a topical anesthetic, has been used as a treatment for another painful rectal condition, ulcerative proctitis (Bjorck et al., 1989, Scandinavian Journal of Gastroenterology, Volume 24, pp. 1061–1072). It has also been recommended to relieve pain sufficiently to permit rectal examination of patients with fissures. However, it is not uncommon for pain relief to be insufficient, so that the physician must resort to anesthesia or intravenous sedation, or wait for improvement with conservative treatment (Janicke & Pundt, 1996, ibid.).

Sucralfate, a polysaccharide originally marketed as a treatment for peptic ulcer disease, has since been used with success for a variety of ulcerative conditions of the skin and of mucosa, including pressure ulcers (bedsores), solitary rectal ulcers (Spiliadis et al., 1989, Gastrointestinal Endoscopy, Volume 35, pp. 131–132), and ulcerative colitis (Riley et al., 1989, Scandinavian Journal of Gastroenterology, Volume 24, pp. 1014–1018). It has not been reported as a treatment for anal fissures. Sucralfate, when applied to a damaged mucosa, forms an adherent film that protects the mucosa and promotes healing (Kochhar et al., 1990; Diseases of the Colon and Rectum, Volume 33, pp. 49–51). In addition, sucralfate lowers local levels of the inflammatory mediator $PGE_2$ (Zahavi et al., 1989; Diseases of Colon and Rectum, Volume 32, pp. 95–98).

SUMMARY OF THE INVENTION

One aspect of the invention is a composition comprising a combination of nitroglycerin and sucralfate. Yet another aspect is a composition comprising a combination of nitroglycerin, lidocaine and sucralfate. These compositions may be combined in a petrolatum base along with a water soluble lubricant such as K-Y™ Jelly. These compositions have analgesic properties.

Another aspect of the invention is a method for treating a painful condition on a body portion which includes providing a composition of nitroglycerin and sucralfate and applying the composition to the body. The composition may also include lidocaine. The compositions may further be mixed with an ointment base such as petrolatum and a water soluble lubricant. These ointments are particularly effective in treating painful conditions of the anal region by applying the composition to the anal region. Painful conditions which respond to the treatment of the invention include anal fissures, thrombosed or inflamed hemorrhoids, pain resulting from ligation of internal hemorrhoids and other chronic anal pain. A suitable water soluble lubricant is K-Y™ Jelly.

DESCRIPTION OF THE PREFERRED EMBODIMENT

As discussed above, nitroglycerin alone and lidocaine alone have been proposed as a treatment for painful conditions in the anal area. The local anesthetic effect of lidocaine is based on a different mechanism of action than the analgesic effect of nitroglycerin. For this reason, I thought these two compounds might have additive or synergistic actions in the treatment of pain of anal fissures and other painful conditions in the anal region. I further reasoned that sucralfate might keep the other two ingredients adherent to the fissure, prolonging their action. Furthermore, the adherent film produced by sucralfate might protect the raw area from irritation by the fecal stream. With these considerations in mind, I prepared a composition which was the combination of nitroglycerin and sucralfate. This formula was 60 grams of K-Y™ Jelly, 15 grams of 2% nitroglycerin ointment, and 6 grams of sucralfate. I prepared a second composition of nitroglycerin, lidocaine and sucralfate in a base of petrolatum and a water soluble lubricant. The formulation was 240 grams petrolatum, 180 grams of K-Y™ Jelly, 60 grams of 2% nitroglycerin ointment, 30 grams of sucralfate and 9.6 grams lidocaine base. The amount of nitroglycerin may be in the range of 30–60 grams. The sucralfate was in powder form.

Case 1

A 49 year old man had a chronic anal fissure, which had persisted for several months, producing chronic rectal pain relieved only by narcotic analgesics. Anoscopy, performed separately by a rectal surgeon and a gastroenterologist, confirmed the presence of a moderately large anal fissure. The surgeon thought that surgery was necessary, and the gastroenterologist proposed cauterization. Neither felt that the fissure would heal without invasive treatment of some kind.

The patient was first treated with nitroglycerin cream, 0.5%. (The cream was prepared by diluting 2% nitroglycerin ointment with a K-Y™ Jelly. This gave substantial but not complete pain relief that lasted about 2 hours, after which the pain gradually returned. Over several weeks, pain was relieved every time the cream was applied, but returned if it was stopped. He was then switched to the combination of nitroglycerin and sucralfate. With this combination, relief lasted 3–4 hours at first, and then lasted longer and longer with repeated applications. Within two weeks, he had full relief applying the cream only twice a day. Within six weeks, the symptoms were totally relieved and the analgesic cream was no longer necessary.

Subsequent Cases 4 subsequent patients, all but one with anoscopically confirmed anal fissures, were treated with the combination of nitroglycerin, lidocaine, and sucralfate, with the expectation of even better relief. (Patient #4 suffered from chronic anal pain of unknown cause.) All 4 of those treated obtained relief, and all chose to continue the medication for several days. Patients were instructed to use the cream as often as they needed for pain relief they found satisfactory. The following table summarizes these patients' reports of their experience with the analgesic cream:

| Patient: Sex and age | 1: ♀ 47 | 2: ♀ 37 | 3: ♂ 69 | 4: ♂ 54 (chronic anal pain) |
|---|---|---|---|---|
| Duration of pain before treatment | 1 week | 2 weeks | 5 weeks | 2 years of discomfort, 5 months of pain |
| Other treatment tried | None | Generic hemorrhoid cream | Anusol ™, Nupercainal ™, sitz baths | None |
| Time from application to relief | 30 minutes | 5 minutes | 30 minutes | 5–10 minutes |
| Percentage of pain remaining after application of the cream | 25% | 50% | 50% | No pain |
| Times a day applied | 2 | 2–3 | 2 | 2 |
| Persistence of benefit | Yes | Yes | Yes | Yes |
| Resolution of painful condition | Yes | Yes | Yes | Partial |
| Time to resolution of condition | 2 weeks | 1 week | 1 week | Severe pain resolved in 1 week |
| Side effects | Headache | Headache, burning sensation | None | Burning sensation |
| Stopped medication because of side effects | No | No | No | No |
| Persistence of side effects | No | Yes | N/A | No |

Five patients, all with anoscopically confirmed fissures, received jars of the analgesic cream, and were instructed to apply it as needed to eliminate their pain. All got complete relief within minutes. The complete relief they obtained contrasted with the partial relief usually reported by patients treated with nitroglycerin ointment alone. Applications about four times daily were adequate to completely control their pain. Three of the patients had been scheduled for surgery to treat their fissures. They had been given the cream 3 to 4 weeks before the date planned for the operation. All three patients cancelled their operations, because they had had sufficient pain relief. One underwent repeat anoscopy, which revealed complete healing of the fissure.

None of the 5 patients required any oral analgesics, sitz baths, or other treatments to relieve pain, as soon as they had access to the nitroglycerin-lidocaine-sucralfate cream.

An additional experiment was performed to establish the effect of the sucralfate. A 64 year old man with severe pain following the rubber band ligation of a hemorrhoid was treated. He had had six weeks of pain prior to the treatment. We treated him on alternate days with either the composition including nitroglycerin, lidocaine and sucralfate or the composition without the sucralfate. He was instructed to reapply the formula any time the pain began to recur. The three ingredient formula gave 90% relief (i.e., pain reduced to 10% of baseline) within fifteen minutes. The patient applied the cream three more times during the next twenty-four hours obtaining satisfactory relief.

The formulation without sucralfate gave less relief, and the pain recurred sooner. The patient applied the two-ingredient (without sucralfate) formula a total of five more times during the next twenty-four hours. Not only did the three-ingredient (with sucralfate) formula act faster, but it was associated with a less severe headache than the two-ingredient formula. The two-ingredient formula may have caused a worse headache because the patient might have used more of it to get relief. Alternatively, the sucralfate in the three-ingredient formula may have slowed the systemic absorption of nitroglycerin.

An additional three patients were treated with various formulations to establish the benefit of sucralfate and to illustrate that the concentration of nitroglycerin needed to treat anal fissure can be lower than that reported in the literature. These cases also show that adding nitroglycerin to the sucralfate-lidocaine combination improves efficacy. The three additional cases are shown in the table below:

| Patient: Sex and age | 1: ♀ 68 | 2: ♂ 81 | 3: ♂ 33 |
|---|---|---|---|
| Diagnosis | Anal fissure | Anal fissure | Inflamed hemorrhoid |
| Duration of pain before treatment | 6 months | 3 months | 2 months |
| Other treatment tried | None | Sitz baths, suppositories; cortisone cream | Desitin ointment |
| Time from application to relief | 30 minutes | 15 minutes | 5 minutes |
| Percentage of pain remaining after application of the cream | 25% | 70% after first application; almost none after 4 weeks | Complete relief |
| Times a day applied | 5 | 2–3 | 3–4 |
| Persistence of benefit | Yes | Yes | Yes |
| Resolution of painful condition | Yes | Yes | Yes, but it recurs occasionally |
| Time to resolution of condition | Not known | 4 weeks | Not known |
| Side effects | None | None | No |
| Stopped medication because of side effects | No | No | No |
| Persistence of side effects | N/A | N/A | N/A |

Patient #1 received the nitroglycerin-lidocaine-sucralfate formula discussed above (formula A) and a formulation without sucralfate (formula B) in the sequence A-B-A over three days. The reported benefit shown in the table above resulted from use of formula A. Formula B was not tolerated; it produced a throbbing headache. This case suggests that sucralfate may actually provide some protection against nitroglycerin-induced headache, perhaps by influencing the absorption of the nitroglycerin.

Patient #2 in the table above received a modified formula with 30 grams of 2% nitroglycerin ointment per 500 grams of the nitroglycerin-lidocaine-sucralfate mixture. The concentration of nitroglycerin in this mixture—0.12%—was lower than the 0.2% concentration reported in recent randomized controlled trials of the use of nitroglycerin as a single agent. Nonetheless, the mixture was efficacious and did not cause headaches (or any other side effects). This case supports the inventor's premise that nitroglycerin in combination with sucralfate and lidocaine is superior to nitroglycerin alone. The combination is efficacious at lower doses of nitroglycerin and the combination is less likely to cause headache.

Patient #3 received formula A and a formulation without nitroglycerin (formula C) in the sequence A-C-A over three days. This formula C (without nitroglycerin) did not give complete relief; the patient estimated that 25% of the pain remained after application. This case supports the relevance of nitroglycerin to the analgesic activity of the mixture, even in conditions other than anal fissure, where the efficacy of nitroglycerin is well established.

Conclusions

A topical analgesic cream or ointment for anal fissures that contains nitroglycerin will be more efficacious if it also contains sucralfate. A cream or ointment containing nitroglycerin, sucralfate, and lidocaine is especially efficacious.

Other anal and rectal conditions, such as inflamed hemorrhoids, produce pain for the same reasons as an anal fissure—a combination of inflammation and spasm of the anal sphincter. Therefore, the combination cream or ointment is expected to be similarly helpful for the pain of those conditions (as demonstrated in patient #3 in the table above). The cream or ointment may also provide relief for pain following rubber band ligation of internal hemorrhoids, as this procedure often leads to sphincter spasm and local inflammation. Finally, the fourth additional case shows that the cream or ointment may be helpful for chronic anal pain of unknown cause.

The triple combination is more likely to produce complete and rapid pain relief than either nitroglycerin or lidocaine alone. It may provide a longer duration of relief than nitroglycerin, as well. Despite the availability of all of the ingredients for many years, there are no reports of the combination being tested as a treatment for the pain of anal fissures or related conditions.

What is claimed is:

1. An analgesic composition comprising nitroglycerin and sucralfate.

2. An analgesic composition comprising nitroglycerin, lidocaine and sucralfate.

3. The composition of claim 1 or 2 wherein the composition further comprises a petrolatum base.

4. The composition of claim 3 further comprising a water soluble lubricant.

5. An analgesic composition comprising nitroglycerin and sucralfate in an ointment or cream base.

6. An analgesic composition comprising nitroglycerin, lidocaine and sucralfate in an ointment or cream base.

7. The analgesic composition of claim 5 or 6 wherein the ointment or cream base further comprises petrolatum and a water soluble lubricant.

8. A method for treating painful conditions of an anal region comprising:

providing a composition comprising nitroglycerin and sucralfate; and applying an effective dose of the composition to the anal region.

9. A method for treating painful conditions of an anal region comprising:

providing a composition comprising nitroglycerin, lidocaine and sucralfate; and applying an effective dose of the composition to the anal region.

10. The method of claim 8 or 9 wherein the step of providing, the composition further comprises an ointment or cream base.

11. The method of claim 10 wherein the step of providing, the ointment or cream base comprises petrolatum and a water soluble lubricant.

12. The method of claim 8 or 9 wherein the painful condition is an anal fissure.

13. The method of claim 8 or 9 wherein the painful condition is thrombosed or inflamed hemorrhoids.

14. The method of claim 8 or 9 wherein the painful condition results from ligation of internal hemorrhoids.

15. The method of any one of claims 8–14, wherein the step of providing, the composition comprises petrolatum, a water soluble lubricant, 2% nitroglycerin ointment, sucralfate and lidocaine.

16. The method of claim 15 wherein the step of providing, the composition comprises petrolatum, a water soluble lubricant, 2% nitroglycerin ointment, sucralfate and lidocaine in a ratio of approximately 24 parts petrolatum: 18 parts lubricant: 6 parts 2% nitroglycerin ointment: 3 parts sucralfate: 1 part lidocaine.

* * * * *